(12) United States Patent
Myagkova et al.

(10) Patent No.: US 8,501,494 B1
(45) Date of Patent: Aug. 6, 2013

(54) METHOD AND DEVICE FOR DETECTING PRIOR DRUG USE, TAKING INFLAMMATION INTO ACCOUNT TO INCREASE TEST'S SPECIFICITY AND REDUCE FALSE POSITIVES

(76) Inventors: Marina Aleksandrova Myagkova, Moscow (RU); Michael Ezrokhi, Raynham, MA (US); Arkady Gershteyn, Newton, MA (US)

( * ) Notice: Subject to any disclaimer, the term of this patent is extended or adjusted under 35 U.S.C. 154(b) by 0 days.

(21) Appl. No.: 13/452,681

(22) Filed: Apr. 20, 2012

(51) Int. Cl.
G01N 33/564 (2006.01)
G01N 33/50 (2006.01)
G01N 33/53 (2006.01)

(52) U.S. Cl.
USPC .......................... 436/507; 435/7.92; 436/518

(58) Field of Classification Search
None
See application file for complete search history.

(56) References Cited

FOREIGN PATENT DOCUMENTS
RU 2296332 C1 3/2007

OTHER PUBLICATIONS

Shankar et al., Journal of Pharmaceutical and biomedical Analysis, 2008; vol. 48 pp. 1267-1281.*
Emery et al., Rheumatol Int (2007) 27:793-806.*
Rauch et al., ("Optimization of Assays" Dec. 2009; retrieved from http://www.biocompare.com/Application-Notes/43605-Optimisation-Of-Assays-Interference-In-Immunoassays-Recognize-And-Avoid/.*
Myagkova et al., Pharmaceutical Chemistry Journal 1999;vol. 33, No. 5 pp. 229-231.*
Verstraete, "Detection times of drugs of abuse in blood, urine, and oral fluid," Ther Drug Monit, 26, 2, pp. 200-205, 2004.
Vandevenne et al., "Detection time of drugs of abuse in urine," Acta Clin Belg., 55, 6, pp. 323-333, 2000.
Virginia department of mines, minerals and energy, "Drug Free Workplace," Downloaded from http://www.dmme.virginia.gov/DM/Announcements%20From%20The%20Chief/DrugFreeWorkplace.pdf on Mar. 3, 2012.
Sachs et al., "Testing for drugs in hair. Critical review of chromatographic procedures since," J.Chromatogr B Biomed Sci Appl., 713, 1, pp. 147-161, 1998.
Jacob et al., Downloaded from http://www.nlm.nih.gov/medlineplus/ency/article/003578.htm on Mar. 3, 2012.
Tintinalli et al., "Toxicology and pharmacology", In: Tintinalli JE, Kelen GD, Stapczynski JS, Ma OJ, Cline DM, eds Emergency Medicine: A Comprehensive Study Guide. 6th ed. Columbus, OH: McGraw-Hill; section 14, 2006.
McPherson et al., "Toxicology and therapeutic drug monitoring", In: McPherson RA, Pincus MR, eds. Henry's Clinical Diagnosis and Management by Laboratory Methods. 21st ed. Philadelphia, Pa: Saunders Elsevier; chap 23, 2006.
Morozova,et al., "The Novel Diagnostic Method for the Early Drug Addiction Reveal" a Power Point Presentation demonstrated on May 10, 2011 at University of Crete, Iraklion, Crete, Greece as part of the Scientific Symposium. Information about PPT being presented is on p. 11 of following website: http://www.biotech.sfu-kras.ru/files/77__program.pdf.
Chandrasoma at al., "Part A, General Pathology, Section II. The Host Response to Injury, Chapter 3 The Acute Inflammatory Response, sub-section Cardinal Clinical Signs". Concise Pathology (3rd edition (Computer file) ed.). New York, N.Y.: McGraw-Hill. ISBN 0838514995. OCLC 150148447. Retrieved Nov. 5, 2008.
Pick, "Inflammation: Causes of Inflammation," downloaded from http://www.womentowomen.com/inflammation/causes.aspx On Mar. 6, 2012.
American Association of Clinical Chemistry. "Quantitative Immunoglobins" Last reviewed Sep. 28, 2010. Last modified Apr. 28, 2011. Downloaded from:http://labtestsonline.org/understanding/analytes/immunoglobulins/tab/test on Mar. 6, 2012.
Todar, "Immune Defense against Bacterial Pathogens: Innate Immunity (p. 4)" Todar's Online Textbook of Bacteriology. Downloaded from: http://textbookbacteriology.net/innate_4.html on Mar. 6, 2012.
Schulz et al., "C-Reactive Protein : Just a Biomarker of Inflammation or a Pathophysiological Player in Myocardial Function and Morphology?" Hypertension , 57, pp. 151-153, 2011. Downloaded from: http://hyper.ahajournals.org/content/57/2/151.
Blake at al., "Tumour necrosis factor-α, inflammatory biomarkers, and Atherogenesis", European Heart Journa,l 23, pp. 345-347, 2002. Downloaded from. eurheartj.oxfordjournals.org/content/23/5/345.full.pdf on Mar. 6, 2012.
http://www.alpco.com/products/hsCRP_ELISA.aspx, downloaded on Mar. 20, 2012.
http://www.alpco.com/products/TNF-alpha_ELISA_Ultrasensitive.aspx. downloaded on Mar. 20, 2012.
http://www.piercenet.com/browse.cfm?fldID=07010181, downloaded on Mar. 20, 2012.
http://www.raybiotech.com/manual/ELISA/ELH-TNFalpha-001.pdf, p. 2, downloaded on Mar. 20, 2012.

* cited by examiner

Primary Examiner — Jacob Cheu
Assistant Examiner — Carmencita M Belei

(57) ABSTRACT

This method and device detects past use of drugs of abuse when the drug substance and its metabolites are no longer present in the body, based on the detection of the antibodies formed in response to said drug, and persist even after this drug and its metabolites are cleared from the body. False positive rate is reduced by screening out subjects with heightened inflammatory state. One embodiment of the invention sets forth the method and device comprising: testing a set of samples for levels of an inflammation biomarker; determining a subset of samples with inflammation biomarker level below a first predetermined threshold; testing samples within the subset of samples for a presence of drug-specific antibodies, for a pre-specified set of drugs; determining which samples within the subset have drug-specific antibody level exceeding pre-specified threshold; and providing an output indicating the samples within the subset having the drug-specific antibodies.

8 Claims, 5 Drawing Sheets

METHOD AND DEVICE FOR DETECTING PRIOR DRUG USE, TAKING INFLAMMATION INTO ACCOUNT TO INCREASE TEST'S SPECIFICITY AND REDUCE FALSE POSITIVES

FIELD

The subject technology generally relates to the area of Medicine, diagnostics and testing in particular.

BACKGROUND

Drug use is currently detected by the analysis of body bodily fluids such as blood and urine, and hair samples. Test methods detect traces of the drug substance or its metabolites in the test samples. These drug traces and metabolites are detectable for a period of about 2 weeks after the drug was used in the fluids. Hair samples may preserve the drug for a longer period. For example, Cocaine is detectable for 3 to 4 days in urine, up to 90 days in hair, 1-2 days in blood.

SUMMARY

In some aspect, the subject technology includes a method and device that tests for past drug use by selectively applying an Enzyme Linked Immunosorbent Assay ELISA-based detection technique on individual's blood or urine sample, even after drug substance and its metabolites may have already been eliminated from the organism and not detectable by current commonly used techniques. The method includes detecting the antibodies that were produced by the human body at the time of drug intake and persist in the body even after all drug substance and metabolites are cleared from the body. The subject technology may be applicable to a wide range of drugs of abuse; multiple drug use may be detected in the same sample simultaneously. In some aspects, the subject technology drastically reduces false positives by screening out those individuals that have heightened level of inflammation as measured by increased plasma or urine levels of C-reactive protein (CRP) and/or Tumor Necrosis Factor alpha (TNF-a). A heightened state of inflammation may cause the majority of false-positive results in the ELISA-based test for the presence of antibodies specific to the drugs of abuse and their metabolites since inflammation generates non-specific increase in antibody levels.

DETAILED DESCRIPTION

In some aspects, the subject technology relates to a machine-implemented method for detecting past drug use. The method includes testing a set of samples for levels of an inflammation biomarker. The method also includes determining a subset of the set of samples, wherein the subset of the set of samples comprises samples having a level of the inflammation biomarker below a first predetermined threshold. The method also includes testing samples within the subset of samples for a presence of drug-specific antibodies. The method also includes determining that one or more samples within the subset having drug-specific antibodies exceeding a threshold correspond to an individual having a history of drug use. The method also includes providing an output indicating the samples within the subset having the drug-specific antibodies.

Optionally, the method includes receiving the set of samples. Optionally, the set of samples includes blood samples. Optionally, the set of samples includes urine samples. Optionally, testing the set of samples for levels of the inflammation biomarker includes applying an Enzyme-Linked Immunosorbent Assay (ELISA) method for testing the stet of samples for levels of the inflammation biomarker. Optionally, the inflammation biomarker includes a C-Reactive Protein (CRP). Optionally, the inflammation biomarker comprises a Tumor Necrosis Factor-Alpha (TNF-A) protein.

In some aspects, the subject technology relates to a device for detecting past drug use. The device includes one or more modules for testing a set of samples for levels of an inflammation biomarker. The device also includes one or more modules for determining a subset of the set of samples. The subset of the set of samples includes samples having a level of the inflammation biomarker below a first predetermined threshold. The device also includes one or more modules for testing samples within the subset of samples for a presence of drug-specific antibodies. The device also includes one or more modules for determining that one or more samples within the subset having drug-specific antibodies exceeding a threshold correspond to an individual having a history of drug use. The device also includes an output for indicating the samples within the subset having the drug-specific antibodies.

Optionally, the device includes an input for receiving the set of samples. Optionally, the set of samples includes blood samples. Optionally, the set of samples includes urine samples. Optionally, testing the set of samples for levels of the inflammation biomarker includes applying an Enzyme-linked immunosorbent assay (ELISA) method for testing the stet of samples for levels of the inflammation biomarker. Optionally, the inflammation biomarker includes a C-Reactive Protein (CRP). Optionally, the inflammation biomarker comprises a Tumor Necrosis Factor-Alpha (TNF-A) protein.

Figure 1:
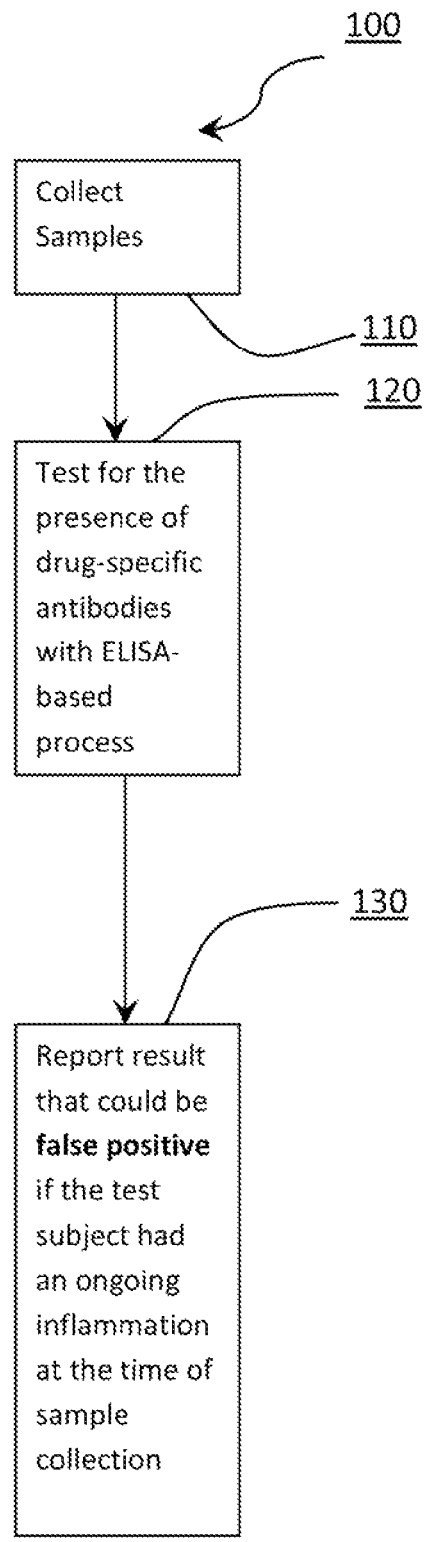
FIG. 1 illustrates the current procedure for ELISA-based detection of past drug use based on serum sample.

FIG. 1 illustrates process 100 for detecting prior drug use. The process 100 begins at step 110, where a serum sample is collected, by operation of a device. The serum sample may be from a subject who is being tested.

In step 120, the device tests for presence of drug-specific antibodies with an Enzyme-linked immunosorbent assay (ELISA)-based technique.

In step 130, the device reports results for a number of different drug substances. The result could be contaminated if the subject being tested is in a heightened state of inflammation, leading to a false positive result(s). After step 130, the process 100 ends.

Figure 2:
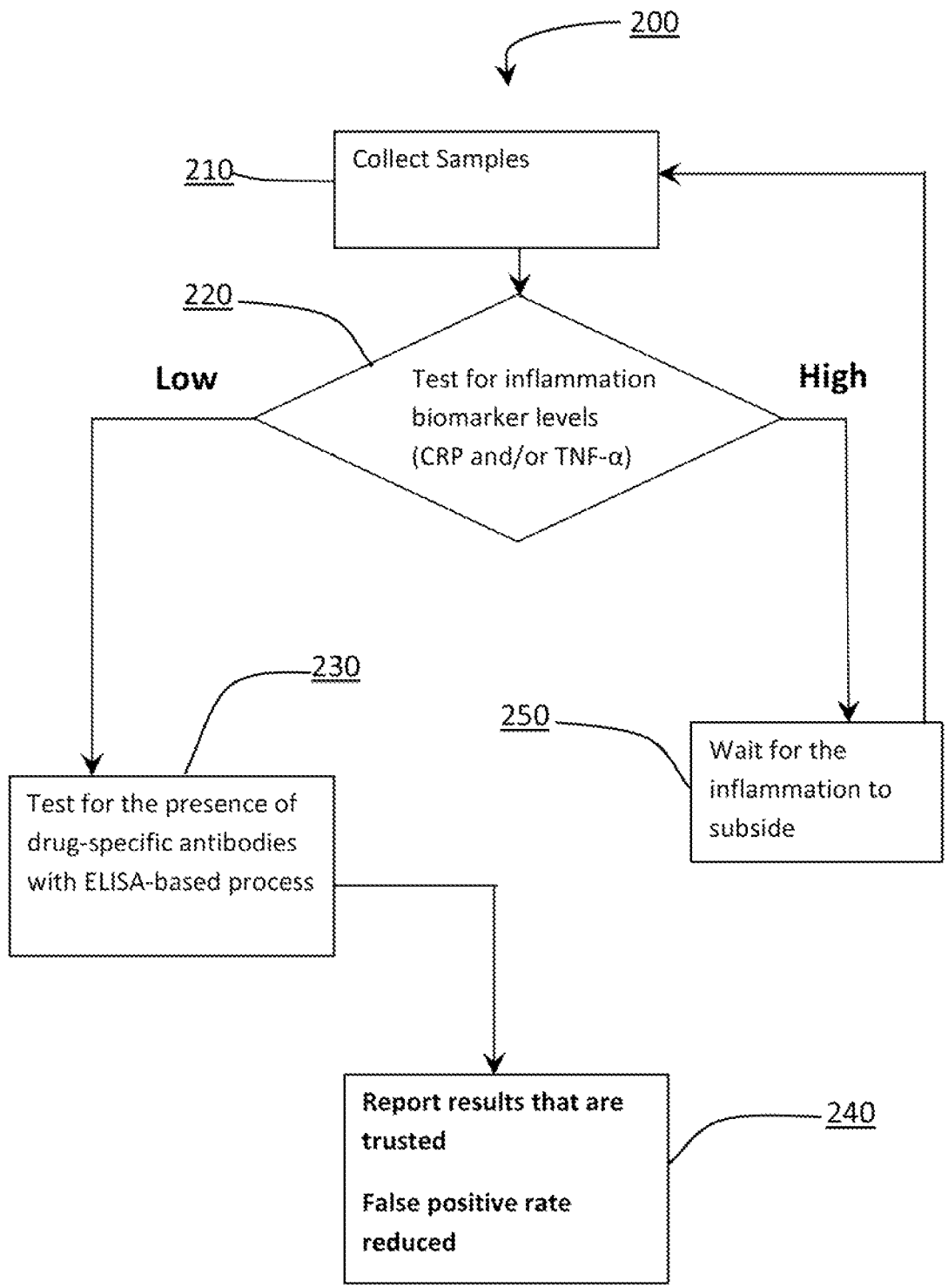
FIG. 2 illustrates the proposed procedure for ELISA-based detection of past drug use based on serum sample, which reduces the false positive rate and increases test specificity, compared to the procedure described in FIG. 1.

FIG. 2 illustrates one example of a process for ELISA-based detection of past drug use based on serum sample, which may, in some implementations, reduce the false positive rate and increase test specificity, compared to the process described in FIG. 1.

The process 200 begins at step 210, where a serum sample is collected from a subject who is being tested.

In step 220, the device evaluates inflammation biomarker levels by ELISA-based technique. Inflammation biomarkers used are the C-Reactive Protein (CRP) and/or the Tumor Necrosis Factor-Alpha (TNF-A). If the inflammation biomarker level is found to be below a pre-determined threshold, the process 200 continues to step 230. If the inflammation biomarker level is found to be at or above the pre-determined threshold, the process 200 continues to step 250.

In step 230, the device tests for the presence of drug-specific antibodies in the serum sample from the test subject with the Enzyme-linked immunosorbent assay ELISA-based technique.

In step 240, the device reports results that may be trusted. The false positive rate is reduced. After step 240, the process 200 ends.

In step 250, the device operator is instructed to suspend the test and repeat the collection of serum sample from the same subject at a later date, when inflammation is expected to subside. After the inflammation subsides, as determined in step 220, the process 200 is allowed to proceed to step 230, followed by step 240 where trustworthy results are obtained and process 200 ends.

Figure 3A:
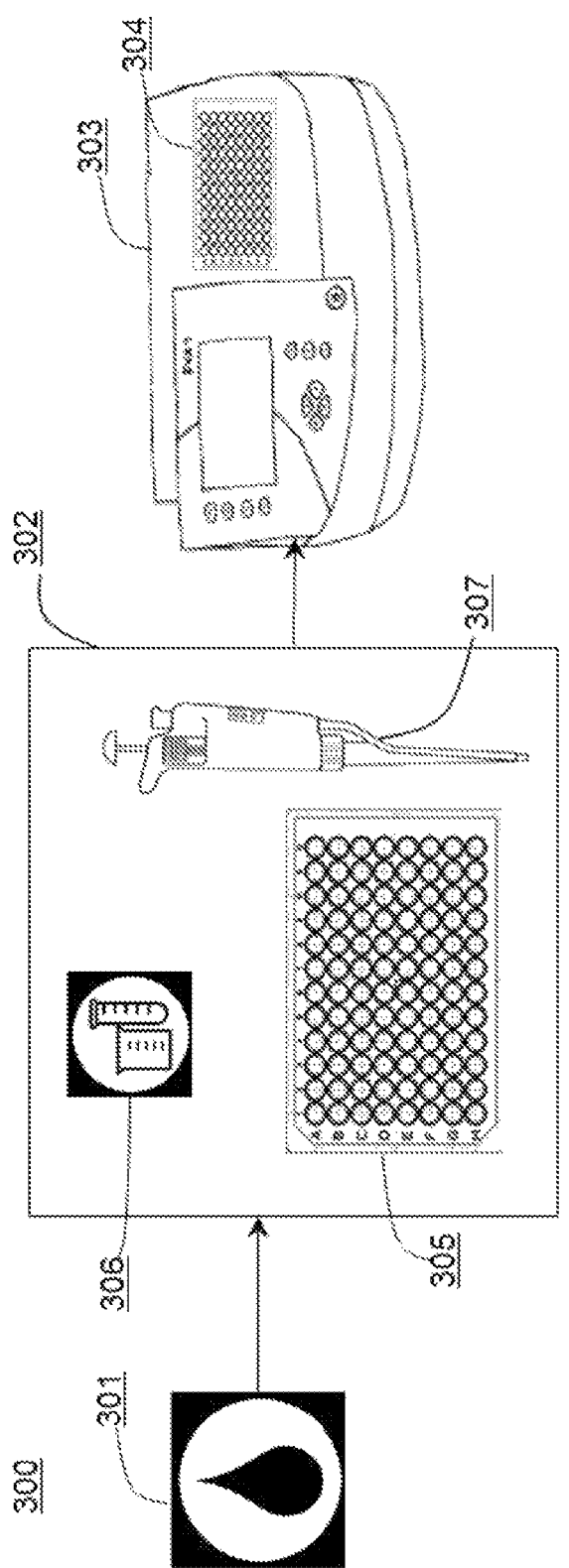
FIG. 3A illustrates a device for detecting prior drug use by ELISA-based technique.

FIG. 3A illustrates a system 300 for detecting prior drug use by ELISA-based technique.

The system 300 may have an input 301 for receiving a serum sample. In some examples, the serum sample is collected from a subject who is being tested, using established blood collection and serum preparation devices and techniques.

The system 300 may also include a device 302. As illustrated, the device 302 includes a polystyrene plate 305 covered with the derivatives of drug substance metabolites immobilized in the wells of the plate, storage tubes with a number of drug-specific reagents 306 for carrying out the ELISA-based technique (e.g., as described in conjunction with FIG. 1 or FIG. 2 above), and a liquid handling device 307 used to measure and move the liquids from storage tubes 306 to the plate 305, as well as distributing serum samples to the plate 305. As illustrated, device 303 is a spectrophotometer, capable of measuring optical density of a solution in the wells of a polystyrene plate at a desired wavelength. Part 304 is the polystyrene plate 305 which has been prepared by addition of the serum sample(s) and drug-specific reagents. Device described in FIG. 3A is suitable for the detection of the antibodies to the following example groups of drugs: opiates, amphetamines, cannabinoids, cocaine, barbiturates, ephedrines. However, the subject technology is not limited by the example groups of drugs set forth above and may be practiced in conjunction with other drugs.

Figure 3B:
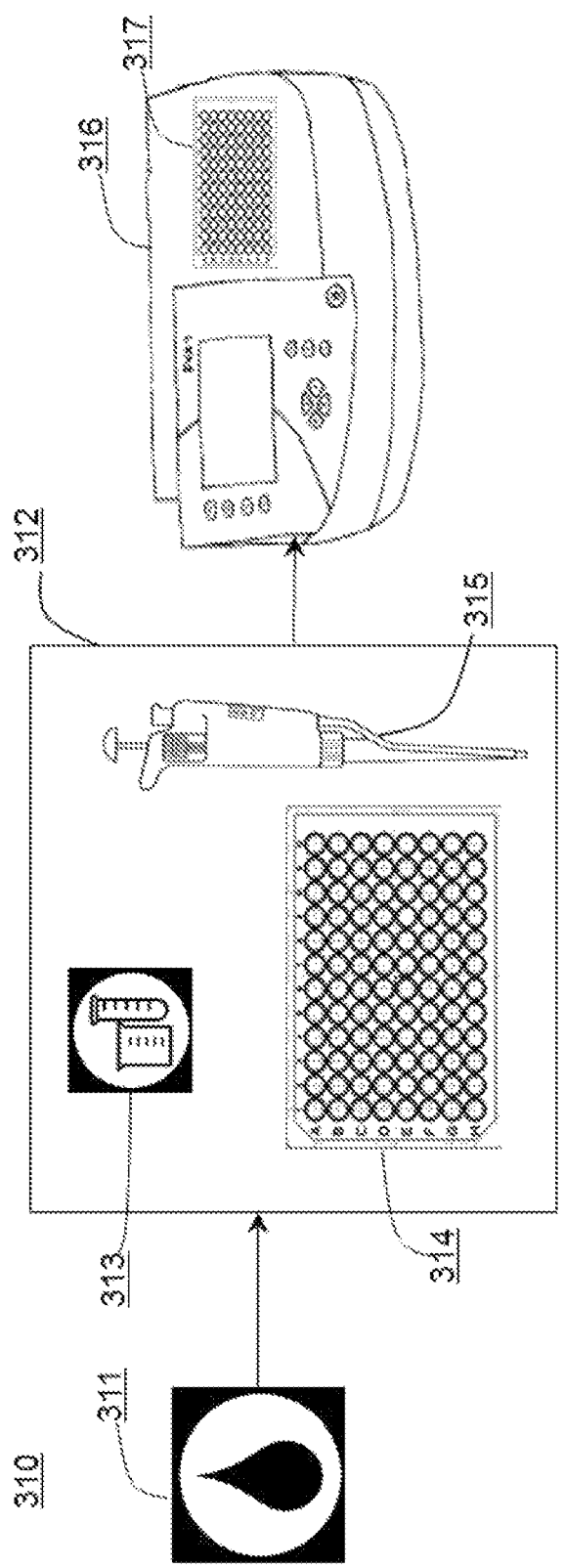
FIG. 3B illustrates a device for measurement of C-reactive protein (CRP) level by ELISA-based technique.

FIG. 3B illustrates a system 310 for measurement of C-reactive protein (CRP) level by ELISA-based technique (e.g., as described in FIGS. 1-2 above).

The system 310 includes an input 311, where a serum sample may be collected, for example, from a subject who is being tested, using established blood collection and serum preparation devices and techniques.

The system 310 may also include a device 312. As illustrated, the device 312 includes a polystyrene plate 314 covered with the antibodies specific to the C-Reactive Protein immobilized in the wells of the plate, storage tubes with a number of CRP-specific reagents 313 for carrying out the ELISA-based technique (e.g., as described in FIGS. 1-2 above), and a liquid handling device 315 used to measure and move the liquids from storage tubes 313 to the plate 314, as well as distributing serum samples to the plate 314. The system 310 may also include a device 316. As illustrated, the device 316 is a spectrophotometer, which may be capable of measuring optical density of a solution in the wells of a polystyrene plate at a desired wavelength. The system 310 also includes a component 317. As illustrated, the component 317 is a polystyrene plate 314 which has been prepared by addition of the serum sample(s) and CRP-specific reagents.

Figure 3C:
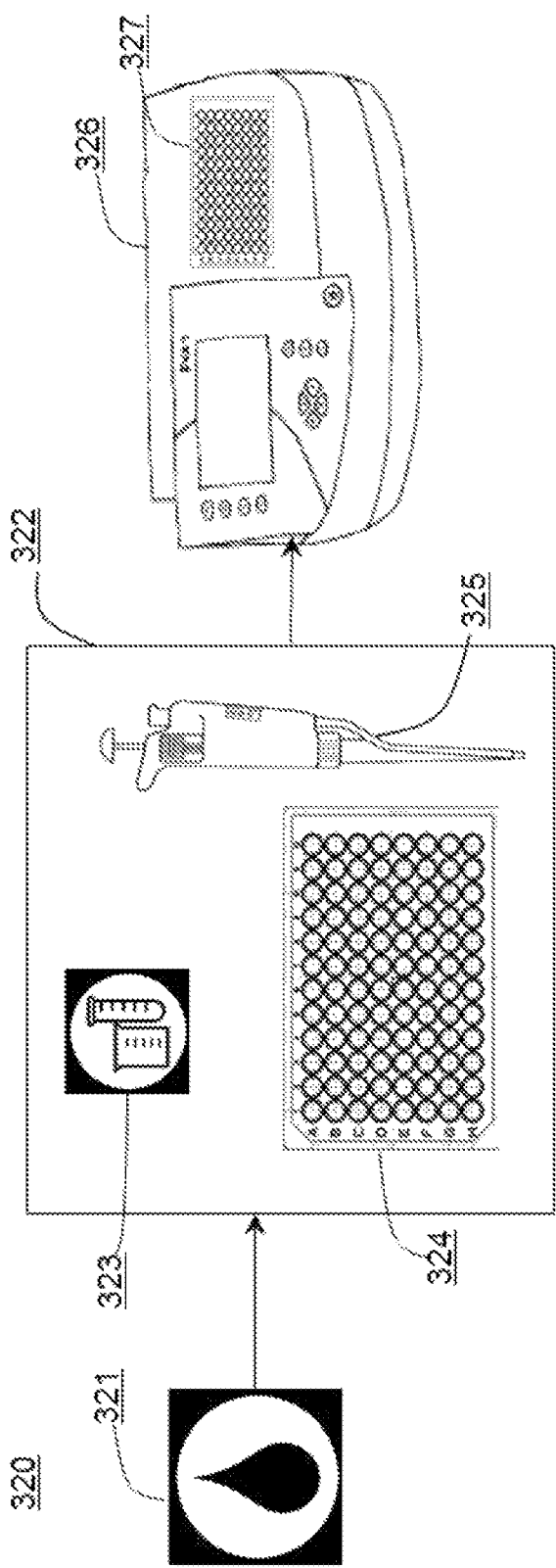
FIG. 3C illustrates a device for measurement of Tumor Necrosis Factor Alpha (TNF-a) by ELISA-based technique.

FIG. 3C illustrates a system 320 for measurement of Tumor Necrosis Factor Alpha (TNF-a) by ELISA-based technique (e.g., as described in FIGS. 1-2 above).

The system 320 includes an input 321, where a serum sample may be collected, for example, from a subject who is being tested, using established blood collection and serum preparation devices and techniques.

The system 320 may also include a device 322. As illustrated, the device 322 includes a polystyrene plate 324 covered with the antibodies specific to the Tumor Necrosis Factor Alpha immobilized in the wells of the plate, storage tubes with a number of TNF-a-specific reagents 323 for carrying out the ELISA-based technique (e.g., as described in FIGS. 1-2 above), and a liquid handling device 325 used to measure and move the liquids from storage tubes 323 to the plate 324, as well as distributing serum samples to the plate 324. The system 320 may also include a device 326. As illustrated, the device 326 is a spectrophotometer, capable of measuring optical density of a solution in the wells of a polystyrene plate at a desired wavelength. The device 326 may also include a component 327. As shown, the component 327 includes a polystyrene plate 324 which has been prepared by addition of the serum sample(s) and TNF-a-specific reagents.

FIGS. 1, 2, and 3A-3C describe some example aspects of the subject technology. However, the subject technology is not limited by these example aspects. Other implementations of the subject technology will be readily apparent to those skilled in the art.

In one aspect, the subject technology may allow to detect past drug use for up to 3 to 5 months in the absence of any clinical symptoms, as well as in the absence of drug and drug metabolites' traces in blood and urine. Thus the subject technology may allow to detect past drug use even in the subjects that have not used controlled substances recently and thus currently free of drugs and drug metabolites.

This subject technology includes, among other things, improvement of Russian Patent No. RU 2296332 C1, granted to Marina Aleksandrovna Myagkova, D.Sc., entitled "Method of early detection of the fact of narcotic substance intake in the absence of clinical signs of drug dependency," and having a priority date of Oct. 28, 2005. Russian Patent No. RU 2296332 C1 is Granted and registered by the Government Registry of the Invention of Russian Federation on Mar. 27, 2007, hereby incorporated by reference in its entirety.

The method described in RU 2296332 C1 is based on the detection of antibodies that are generated by the human body in response to drug intake. ELISA technique is applied to detect the presence of antibodies specific to a drug in urine and plasma samples.

The method of RU 2296332 C1, while it allows to detect the fact of past drug use for up to 3 to 5 months after the last drug use episode, suffers from a high rate of false positive, 5% to 7%.

Specificity of the current method of anti-drug antibody detection is currently 93-95%, depending on the substance of abuse. Specificity (SP) is defined according to equation (1) below.

$$SP = \frac{TP}{TP + FP} \cdot 100\% \qquad (1)$$

Where TP is true positive, i.e. a past drug user identified as such by the test

FP is false positive, i.e. a person who did have contact with the drug but identified as a past drug user.

In other words, out of a 100 tested subjects, 5 to 7 will be falsely accused of past drug use.

False positives are mostly due to heightened state of the test subject's inflammatory response to factors unrelated to drug use but affecting the immune response, such as a cold, flu, pregnancy, injury. However, false positives may be due to other factors also. Inflammation tends to increase antibody production for most antibodies, including the ones that cross-react with the ELISA-based detection system used in RU 2296332 C1.

Independent measurement of a biomarker indicative of heightened inflammatory state allows to identify and filter out the subjects most likely to test as false positive. These subjects' test should be delayed until such time as inflammation subsides to pre-determined threshold.

Example of such a biomarker is CRP (C-Reactive Protein), may be elevated in the subjects with the ongoing inflammation. Other inflammatory biomarkers may also be used, including TNF-a (Tumor necrosis factor-alpha). ELISA-based method for CRP measurement in a sample of human serum, plasma or urine is commercially available. ELISA-based method for TNF-a measurement in a sample of human serum, plasma or urine is commercially available.

The subject technology, among other things, may reduce the false positive rate, thus increasing specificity and allowing for the widespread use of technique in wide spectrum application. Applications of the subject technology include, among other things, screening of potential employees and monitoring current employees, monitoring drug rehab patients, monitoring students in schools and colleges, and any other application where potential drug addiction could be especially detrimental.

Any method suitable to a protein detection in a body fluid such as blood or urine may be used to assess the level of inflammatory biomarker. ELISA method similar to the one described in RU 2296332 C1 may be used. Subjects whose biomarker levels exceed the specified threshold may, in some implementations of the subject technology, be excluded from the subsequent drug testing until a later time when the inflammation subsides.

As used herein, any reference to the word "one" or "a" may encompass one or more. For example, "a device" may encompass one or more devices.

Several different example aspects of the subject technology are described above. However, the subject technology is not limited by these example aspects. Other example aspects, with which the subject technology may be implemented, will be readily apparent to persons skilled in the art. The subject technology is limited only by the following claims.

The invention claimed is:

1. A machine-implemented method for detecting past drug abuse, the method comprising:
   testing a set of samples for levels of an inflammation biomarker;
   determining a subset of the set of samples, wherein the subset of the set of samples comprises samples having a level of the inflammation biomarker below a first predetermined threshold and wherein a level of the biomarker above the first threshold is indicative of a heightened level of inflammation in a subject;
   testing samples within the subset of samples for a presence of drug-specific antibodies;
   determining that one or more samples within the subset having drug-specific antibodies exceeding a threshold correspond to an individual having a history of drug abuse; and
   providing an output indicating the samples within the subset having the drug-specific antibodies, wherein drug-specific antibodies are produced by the subject in response to drug abuse.

2. The method of claim 1, further comprising:
   receiving the set of samples.

3. The method of claim 1, wherein the set of samples comprises blood samples.

4. The method of claim 1, wherein the set of samples comprises urine samples.

5. The method of claim 1, wherein testing the set of samples for levels of the inflammation biomarker comprises applying an Enzyme-linked immunosorbent assay (ELISA) method for testing the stet of samples for levels of the inflammation biomarker.

6. The method of claim 1, wherein the inflammation biomarker comprises a C-Reactive Protein (CRP).

7. The method of claim 1, wherein the inflammation biomarker comprises a Tumor Necrosis Factor-Alpha (TNF-A) protein.

8. The method of claim 1, further comprising:
   determining an additional subset of the set of samples, wherein the additional subset of the set of samples comprises samples having a level of the inflammation biomarker above the first predetermined threshold; and
   delaying testing samples within the additional subset of samples for a presence of drug-specific antibodies until the level of the inflammation biomarker in the samples within the additional subset of samples subsides to the first predetermined threshold.

* * * * *